United States Patent
Kim et al.

(10) Patent No.: US 8,666,197 B2
(45) Date of Patent: Mar. 4, 2014

(54) METHOD OF GENERATING IMAGE, APPARATUS FOR PERFORMING THE SAME, DIAGNOSIS SYSTEM, AND MEDICAL IMAGE SYSTEM

(75) Inventors: Kyu-hong Kim, Suwon-si (KR); Sung-chan Park, Suwon-si (KR); Jung-ho Kim, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 192 days.

(21) Appl. No.: 13/243,286

(22) Filed: Sep. 23, 2011

(65) Prior Publication Data

US 2012/0269408 A1 Oct. 25, 2012

(30) Foreign Application Priority Data

Apr. 22, 2011 (KR) .................. 10-2011-0037981

(51) Int. Cl.
 *G06K 9/32* (2006.01)
 *G06K 9/00* (2006.01)
(52) U.S. Cl.
 USPC .......................................... 382/299; 382/128
(58) Field of Classification Search
 USPC .................. 382/128, 131, 132, 299
 See application file for complete search history.

(56) References Cited

U.S. PATENT DOCUMENTS

| 6,442,289 B1 | 8/2002 | Olsson et al. | |
| 7,725,169 B2 * | 5/2010 | Boppart et al. | 600/473 |
| 8,208,709 B2 * | 6/2012 | Ding et al. | 382/131 |
| 2005/0288588 A1 | 12/2005 | Weber et al. | |
| 2007/0083114 A1 | 4/2007 | Yang et al. | |

FOREIGN PATENT DOCUMENTS

| EP | 1 300 690 A1 | 4/2003 |
| JP | 2005-296331 | 10/2005 |
| JP | 2009-082469 | 4/2009 |
| JP | 2009-153918 | 7/2009 |
| KR | 10-2008-0034660 | 4/2008 |
| KR | 10-2008-0044737 | 5/2008 |
| KR | 10-2009-0042153 | 4/2009 |
| KR | 10-2010-0036422 | 4/2010 |

OTHER PUBLICATIONS

European Search Report dated Jul. 24, 2012, issued in counterpart European Patent Application No. 12158154.0; 7 pages.
Holfort, et al. "Adaptive receive and transmit apodization for synthetic aperture ultrasound imaging." Ultrasonics Symposium (IUS), 2009 IEEE International. (4 pages, in English).

* cited by examiner

*Primary Examiner* — Yon Couso
(74) *Attorney, Agent, or Firm* — NSIP Law (57) ABSTRACT

A diagnosis image generation apparatus is provided. The diagnosis image generation apparatus includes a low resolution image signal synthesis unit configured to synthesize each of a plurality of low resolution image signals by using a signal reflected from a subject, a weight calculation unit configured to calculate a weight, which is used to synthesize a high resolution image signal, with a signal value which corresponds to each of positions of some pixels among a plurality of signal values corresponding to respective positions of a plurality of pixels forming each of the synthesized low resolution image signals, and a high resolution image signal synthesis unit configured to synthesize the high resolution image signal by applying the calculated weight to each of the low resolution image signals.

20 Claims, 7 Drawing Sheets

METHOD OF GENERATING IMAGE, APPARATUS FOR PERFORMING THE SAME, DIAGNOSIS SYSTEM, AND MEDICAL IMAGE SYSTEM

CROSS-REFERENCE TO RELATED APPLICATIONS

This application claims the benefit of Korean Patent Application No. 10-2011-0037981, filed on Apr. 22, 2011, in the Korean Intellectual Property Office, the entire disclosure of which is incorporated herein by reference for all purposes.

BACKGROUND

1. Field

The following description relates to a method of generating an image, an apparatus for performing the same, a diagnosis system, and a medical image system.

2. Description of the Related Art

An image system using a synthetic aperture technique synthesizes a plurality of low resolution image signals and synthesizes a high resolution image signal, in which case a transmission apodization weight may be applied. In applying the transmission apodization weight, a data-independent technique that accumulates and adds values of pixels forming low resolution images regardless of an input signal may be applied. Since a diagnosis image generated by the data-independent technique may not have good contrast or resolution, a data-dependent technique that calculates an apodization weight in all pixels forming low resolution images may be used for acquiring a high definition image. In a diagnosis image generated by the data-dependent technique, high resolution performance may be guaranteed, but an increase in the number of operations occurs rapidly and thus an image, for example, a diagnosis image, is difficult to generate.

SUMMARY

According to an aspect, a diagnosis image generation apparatus is provided. The diagnosis image generation apparatus includes a low resolution image signal synthesis unit configured to synthesize each of a plurality of low resolution image signals by using a signal reflected from a subject, a weight calculation unit configured to calculate a weight, which is used to synthesize a high resolution image signal, with a signal value which corresponds to each of positions of some pixels among a plurality of signal values corresponding to respective positions of a plurality of pixels forming each of the synthesized low resolution image signals, and a high resolution image signal synthesis unit configured to synthesize the high resolution image signal by applying the calculated weight to each of the low resolution image signals.

The weight calculation unit may divide each of the low resolution image signals into a plurality of regions, and calculate a weight with a signal value corresponding to a position of one pixel included in each of the regions, and the high resolution image signal synthesis unit may apply the calculated weight to a region including the pixel corresponding to the signal value which has been used to calculate the weight.

The weight calculation unit may calculate the weight for the signal value which corresponds to each of the positions of some pixels included in each of the low resolution image signals, in a minimum variance technique.

The weight calculation unit may generate a covariance matrix for a signal value which corresponds to each of the positions of some pixels included in each of the low resolution image signals, calculate an inverse of the generated covariance matrix, and calculate a weight with the calculated inverse of the covariance matrix.

The weight calculation unit may include a weight storage configured to store the calculated weight, and a weight updater configured to calculate a weight which is used to synthesize the high resolution image signal, and configured to update the weight, stored in the weight storage, to the calculated weight.

The high resolution image signal synthesis unit may at least once apply the weights, stored in the weight storage, to a signal value other than the signal values, corresponding to each of the positions of some pixels which have been used to calculate the weight, among signal values corresponding to respective positions of the pixels forming the low resolution image signals.

The weight may correspond to an apodization weight.

In another aspect, a diagnosis system is provided. The diagnosis system includes a probe configured to transmit/receive a signal to/from a subject by using a plurality of transducers, and a diagnosis image generation apparatus synthesizing each of a plurality of low resolution image signals with signals received from the probe, configured to synthesize a high resolution image signal by applying a weight, which is calculated with a signal value which corresponds to each of positions of some pixels among a plurality of signal values corresponding to respective positions of a plurality of pixels forming each of the synthesized low resolution image signals, to each of the low resolution image signals, and configured to output the synthesized high resolution image signal as a diagnosis image.

The diagnosis image generation apparatus may divide each of the low resolution image signals into a plurality of regions, and calculate a weight with a signal value corresponding to a position of one pixel included in each of the regions, and may apply the calculated weight to a region including the pixel corresponding to the signal value which has been used to calculate the weight.

In yet another aspect, a medical image system is provided. The medical image system includes a diagnosis image generation apparatus configured to synthesize each of a plurality of low resolution image signals by using a signal reflected from a subject, configured to synthesize a high resolution image signal by applying a weight, which is calculated with a signal value which corresponds to each of positions of some pixels among a plurality of signal values corresponding to respective positions of a plurality of pixels forming each of the synthesized low resolution image signals, to each of the low resolution image signals, and configured to output the synthesized high resolution image signal as a diagnosis image, and a display unit configured to display the output diagnosis image.

The diagnosis image generation apparatus may divide each of the low resolution image signals into a plurality of regions, and calculate a weight with a signal value corresponding to a position of one pixel included in each of the regions, and may apply the calculated weight to a region including the pixel corresponding to the signal value which has been used to calculate the weight.

In yet another aspect, a method of generating a diagnosis image is provided. The method includes receiving a signal reflected from a subject, synthesizing each of a plurality of low resolution image signals by using the received signal, calculating a weight, which is used to synthesize a high resolution image signal, with a signal value which corresponds to each of positions of some pixels among a plurality of signal values corresponding to respective positions of a plurality of pixels forming each of the synthesized low resolution image signals, and synthesizing the high resolution image signal by applying the calculated weight to each of the low resolution image signals.

The calculating of the weight may divide each of the low resolution image signals into a plurality of regions, and calculate a weight with a signal value corresponding to a position of one pixel included in each of the regions, and the synthesizing of the high resolution image signal may apply the calculated weight to a region including the pixel corresponding to the signal value which has been used to calculate the weight.

The calculating of the weight may calculate the weight for the signal value which corresponds to each of positions of some pixels included in each of the low resolution image signals, in a minimum variance technique.

The calculating of the weight may generate a covariance matrix for a signal value which corresponds to each of positions of some pixels included in each of the low resolution image signals, calculate an inverse of the generated covariance matrix, and calculate a weight with the calculated inverse of the covariance matrix.

The calculating of the weight may include calculating the weight which is used to synthesize the high resolution image signal, storing the calculated weight, and updating the stored weight to the calculated weight.

The synthesizing of the high resolution image signal may at least once apply the stored weights to a signal value other than the signal values, corresponding to each of the positions of pixels which have been used to calculate the weight, among signal values corresponding to respective positions of the pixels forming the low resolution image signals.

The weight may correspond to an apodization weight.

The method may further include displaying the synthesized high resolution image signal as a diagnosis image.

A non-transitory computer-readable storage medium may store a computer program for executing the method.

Other features and aspects may be apparent from the following detailed description, the drawings, and the claims.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

Figure 1:
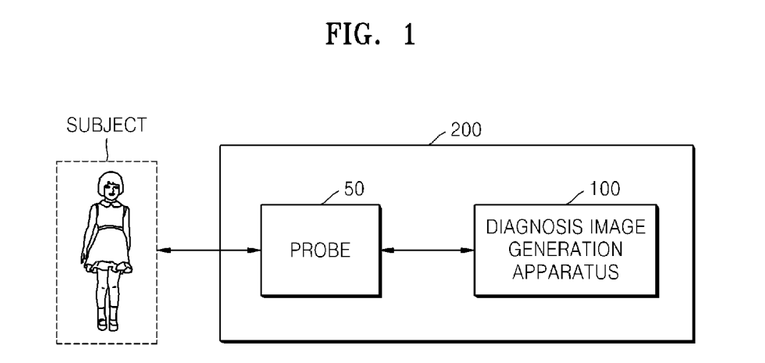
FIG. 1 is a diagram illustrating an example of a use environment of a diagnosis system.

FIG. 1 is a diagram illustrating an example of a use environment of a diagnosis system 200. Referring to FIG. 1, the diagnosis system 200 includes a probe 50 and a diagnosis image generation apparatus 100. The diagnosis image generation apparatus 100 transmits/receives a signal to/from the probe 50, and generates a diagnosis image for a subject.

The probe 50 transmits a signal to the subject and receives a signal reflected from the subject with a plurality of transducers.

The diagnosis image generation apparatus 100 synthesizes a plurality of low resolution image signals by using signals received from the transducers, synthesizes a high resolution image signal by using the synthesized low resolution image signals, and generates an image, such as, a diagnosis image, by using the synthesized high resolution image signal, according to, for example, a synthetic aperture technique. In this case, a signal reflected from each of the transducers of the probe 50 may be a signal reflected from the subject.

Herein, the synthetic aperture technique refers to one or more high resolution image signals being synthesized by synthesizing a plurality of low resolution image signals. A signal value corresponding to each of the positions of pixels forming the high resolution image may be generated according to signal values corresponding to respective positions of pixels forming each of the low resolution images.

A low resolution image signal refers to a signal that forms and corresponds to a low resolution image, and a high resolution image signal refers to a signal that forms and corresponds to a high resolution image.

Signal values corresponding to respective positions of pixels forming the low resolution image may be information regarding a subject that a signal reflected from the subject indicates. For example, a signal value corresponding to each of the positions of pixels indicates a signal value corresponding to the brightness of each of the positions of pixels forming the low resolution image.

Since the absolute value of a size of a signal reflected from the subject may indicate brightness of the signal reflected from the subject, it is understood as being within the scope of the teachings herein that brightness information regarding the subject may be expressed as the size of the signal reflected from the subject. Therefore, the signal values corresponding to the respective positions of the pixels forming the low resolution image may be the brightness information regarding the subject that the signal reflected from the subject indicates.

As an example of an ultrasonic signal, a brightness difference between signal values for pixels in the same position of each low resolution image is a signal value difference that is estimated by calculating an estimation value, where the ultrasonic signal is reflected from a particle in a medium, in beamforming. Therefore, the synthetic aperture technique may be a method that reciprocally supplements the brightness difference to synthesize a high resolution image signal.

A signal value for a pixel in the same position of each low resolution image may be a signal value that indicates brightness information regarding the same point of the subject. In this case, a plurality of signal values (which indicate brightness information regarding the same point of the subject) for pixels in the same position of each low resolution image may not be the same. Such a difference may be caused by a difference due to an offset according to where each of the transducers transmits a signal to the subject. In response to the each transducer transmitting a signal to the subject, an offset according to where each of transducers in different positions transmits a signal occurs for the subject, and thus, a difference between signal values for the same position of each low resolution image occurs.

Therefore, the synthetic aperture technique reciprocally supplements the brightness difference to synthesize a high resolution image signal.

The diagnosis image generation apparatus 100 provides a weight to each of a plurality of low resolution image signals to synthesize a high resolution image signal. The weight provided to each of the low resolution image signals is calculated with signal values, corresponding to respective positions of some pixels, among signal values for pixels forming each of the low resolution images. As a non-limiting example, the weight may be an apodization weight that is applied in the synthetic aperture technique or a weight that is used in a fast apodization method.

In this way, the diagnosis image generation apparatus 100 applies a weight that is calculated with signal values, corresponding to respective positions of some pixels, among signal values corresponding to respective positions of pixels forming each of the low resolution images. Accordingly, the diagnosis image generation apparatus 100 may reduce the number of operations and generate a high definition diagnosis image for a subject.

Figure 2:
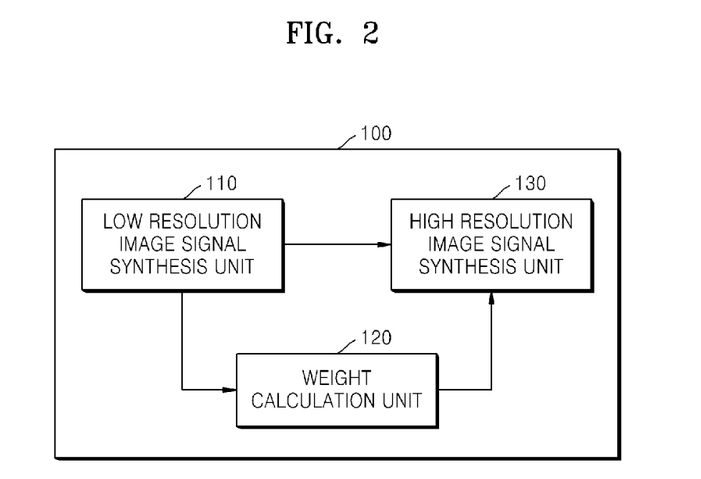
FIG. 2 is a diagram illustrating an example of a diagnosis image generation apparatus.

FIG. 2 is a diagram illustrating an example of the diagnosis image generation apparatus 100. Referring to FIG. 2, the diagnosis image generation apparatus 100 includes a low resolution image signal synthesis unit 110, a weight calculation unit 120, and a high resolution image signal synthesis unit 130.

In the diagnosis image generation apparatus 100 of FIG. 2, elements associated with this example are illustrated. It is understood as being within the scope of the teachings herein that the diagnosis image generation apparatus 100 may further include general elements other than the elements of FIG. 2.

Moreover, the low resolution image signal synthesis unit 110, the weight calculation unit 120, the high resolution image signal synthesis unit 130 of the diagnosis image generation apparatus 100 in FIG. 2, or any combination thereof may be implemented by one or more processors. The processor may be implemented by an array of logic gates, or implemented by the combination of a general microprocessor and a memory storing a program executable by the microprocessor. Also, it is understood to those skilled in the art that the elements of the diagnosis image generation apparatus 100 may be implemented with other types of hardware.

The diagnosis image generation apparatus 100 may generate a high resolution image signal for a subject, and the generated high resolution image signal may be a diagnosis image of the subject.

The low resolution image signal synthesis unit 110 synthesizes each of a plurality of low resolution image signals by using a signal reflected from the subject. It is understood that the synthesizing of a low resolution image signal by the low resolution image signal synthesis unit 110 may be a case of substantially generating the low resolution image signal and moreover a case in which signal values are generated to correspond to respective positions of pixels forming the low resolution image.

It is further understood that the low resolution image signal synthesis unit 110 may include a beamformer (not shown), or synthesize each of a plurality of low resolution image signals by using a signal outputted from the beamformer. As a non-limiting example, the beamformer may be an adaptive beamformer that forms a reception beam for outputting signal values corresponding to respective positions of pixels forming the low resolution image.

Also, the low resolution image signal synthesis unit 110 receives a signal reflected from the subject with the transducers, and synthesizes each of a plurality of low resolution image signals by using a signal value that is calculated from each of the signals received from the transducers.

For example, where an M number of transducers receive a signal reflected from a subject, an operation performed by the low resolution image signal synthesis unit 110 may be expressed as Equation (1).

$$l_i(\vec{r}_p) = \sum_{m=0}^{M-1} w^*_{m,i}(\vec{r}_p) y_{m,i}(\Delta_{m,i}(\vec{r}_p)) \quad (1)$$

where $\vec{r}_p$ is a focal point of a received signal that is transmitted from the transducer and reflected from the subject, $l_i(\vec{r}_p)$ is a size value of a signal corresponding to a pixel in a position $\vec{r}_p$ of an $i^{th}$ low resolution image, $w^*_{m,i}(\vec{r}_p)$ is a beamforming coefficient that is applied to a pixel in the position $\vec{r}_p$ among signal values corresponding to respective positions of pixels forming the $i^{th}$ low resolution image based on a signal received by an $m^{th}$ transducer, a superscript * is a conjugate complex number, $y_{m,i}(\ )$ is a signal, received by the $m^{th}$ transducer, for the $i^{th}$ low resolution image, $\Delta_{m,i}$ is a sampling time for signals, received by the $m^{th}$ transducer, for the $i^{th}$ low resolution image, and $y_{m,i}(\Delta_{m,i}(\vec{r}_p))$ is a signal that is obtained by applying a delay value to a pixel in the position $\vec{r}_p$ for a signal, received by the $m^{th}$ transducer, for the $i^{th}$ low resolution image.

Therefore, the low resolution image signal synthesis unit 110 performs an operation such as Equation (1) to synthesize a plurality of low resolution image signals by using signals that are respectively received by the M transducers.

The weight calculation unit 120 calculates a weight, which is used to synthesize a plurality of low resolution image signals, with a signal value corresponding to each of the positions of some pixels among signal values corresponding to respective positions of pixels forming each of the low resolution images that have been synthesized by the low resolution image signal synthesis unit 110, respectively.

As an example, a signal value corresponding to each of the positions of some pixels among signal values corresponding to respective positions of pixels forming each of the low resolution image signals is provide, in response to the number of signal values corresponding to respective positions of all pixels forming each of the low resolution image signals being A number, a signal value corresponding to each of the positions of some pixels may be equal to or greater than one or equal to or less than A-1 number. Herein, the signal value corresponding to each of the positions of some pixels may be set substantially identical to each of the low resolution image signals.

At this point, the weight calculation unit 120 divides a low resolution image into a plurality of regions and calculates a weight with any one beamformed signal value included in each of the regions. The weight calculation unit 120 allows the calculated weight to be applied to all regions or some regions.

In this case, the beamformed signal value indicates a signal value corresponding to a position of any one of the pixels forming a low resolution image, and some regions indicate regions including a signal value that is used to calculate a weight.

Therefore, the weight calculation unit 120 divides a low resolution image into a plurality of regions and calculates a weight with a signal value that corresponds to a position of any one pixel included in each region. The calculated weight is applied to a region including a pixel corresponding to a signal value that is used to calculate the weight. This will be described below with reference to FIG. 3.

For example, to calculate a weight, the weight calculation unit 120 calculates a weight that is used to synthesize a high resolution image signal, by applying a minimum variance technique for a signal value that corresponds to each of the positions of some pixels included in respective low resolution images.

The minimum variance technique refers to a method that calculates a weight, which allows a variance value of a beamforming result to be minimized, without distortion of a target direction in calculating of the weight. The minimum variance technique is understood to those skilled in the art, and accordingly, description thereof is not provided for conciseness.

The weight calculation unit 120 generates a covariance matrix for a signal value that corresponds to each of the positions of some pixels included in respective low resolution images, calculates the inverse of the calculated covariance matrix, and calculates a weight with the inverse of the generated covariance matrix.

As an example, the weight calculation unit 120 may perform an operation such as Equation (2) and thus calculate a weight that is used to synthesize a high resolution image signal.

$$\alpha = \frac{\hat{R}^{-1}}{e^H \hat{R}^{-1} e} \quad (2)$$

where $\alpha$ is a weight that is applied for each of the low resolution image signals, e is a steering vector, $e^H$ is a Hermitian transpose for the steering vector, $\hat{R}^{-1}$ is the inverse of a covariance matrix for a signal value corresponding to each of the positions of some pixels among signal values that correspond to respective positions of pixels forming low resolution images.

As another example, the steering vector e is for controlling a phase of a signal that is transmitted from a probe (not shown) to a subject. Assuming that a time delay value for beamforming has been applied beforehand according to a direction, the steering vector is configured as 1 because a beamforming coefficient is a real value. Herein, a size of the steering vector is the same as the number of low resolution image signals.

As an example, using a matrix notation, in response to three low resolution image signals being generated, the steering vector may be expressed as Equation (3).

$$e = [1\ 1\ 1]^T \quad (3)$$

Moreover, a covariance $R(r_p)$ may be expressed as Equation (4).

$$R(\vec{r_p}) = l_{LRI}(\vec{r_p}) l_{LRI}(\vec{r_p})^H \quad (4)$$

where $R(\vec{r_p})$ is a covariance for a signal value corresponding to a pixel in a position $\vec{r_p}$ among signal values forming a plurality of low resolution image signals, $l_{LRI}(\vec{r_p})$ is a size value of a signal corresponding to a pixel in a position $\vec{r_p}$ among signal values corresponding to respective positions of pixels forming the low resolution image signals, and $l_{LRI}(\vec{r_p})^H$ indicates a Hermitian transpose for $l_{LRI}(\vec{r_p})$.

Herein, $\vec{r_p}$ may be each of positions of some pixels among pixels forming respective low resolution images. To describe a case of $\vec{r_p}$ is (j, k) as an example, $l_{LRI}(j,k)$ indicates size values of a signal corresponding to a coordinate (j, k) of each of the low resolution image signals.

As an example, using a matrix notation, three low resolution image signals may be expressed as Equation (5).

$$LRI_1 = \begin{bmatrix} p_{11} & p_{12} & p_{13} \\ p_{14} & p_{15} & p_{16} \\ p_{17} & p_{18} & p_{19} \end{bmatrix}$$

$$LRI_2 = \begin{bmatrix} p_{21} & p_{22} & p_{23} \\ p_{24} & p_{25} & p_{26} \\ p_{27} & p_{28} & p_{29} \end{bmatrix}$$

$$LRI_3 = \begin{bmatrix} p_{31} & p_{32} & p_{33} \\ p_{34} & p_{35} & p_{36} \\ p_{37} & p_{37} & p_{39} \end{bmatrix} \quad (5)$$

where each of the elements ($p_{11}$ to $p_{19}$, $p_{21}$ to $p_{29}$, and $p_{31}$ to $p_{39}$) configuring the respective matrixes may be a signal value corresponding to a position of each of pixels forming a low resolution image.

To describe a case where (j, k) is (2, 2) as an example, $l_{LRI}(2,2)$ may be expressed as Equation (6).

$$l_{LRI}(2,2) = [p_{15}\ p_{25}\ p_{35}] \quad (6)$$

Therefore, a covariance matrix for a signal value corresponding to a position of a pixel (2, 2) among pixels forming a plurality of low resolution images may be expressed as Equation (7).

$$R(2,2) = [p_{15}\ p_{25}\ p_{35}]^T \cdot [p_{15}\ p_{25}\ p_{35}] \quad (7)$$

Therefore, by performing the above-described operation, the weight calculation unit 120 may generate a covariance matrix for a signal value corresponding to each of the positions of some pixels among signal values corresponding to respective positions of pixels forming each of a plurality of low resolution images, calculate the inverse of the generated covariance matrix, and calculate a weight, which is used to synthesize a high resolution image signal, with the steering vector and the inverse of the calculated covariance matrix. Also, a sub-array method is understood to those skill in the art and thus, its description is not provided for conciseness.

In calculating of the inverse of the covariance matrix, the weight calculation unit 120 may use a diagonal loading technique for guaranteeing stability. As an example, the weight calculation unit 120 may further perform an operation such as Equation (8) that is used to calculate a covariance for calculating a weight.

$$\hat{R} = R + \gamma I \qquad (8)$$

where $\hat{R}$ is a covariance with enhanced stability for a plurality of low resolution image signals, R is a covariance for the low resolution image signals, γ is a small scalar value, for example, may be 0.01, and I is an identity matrix.

As an example of a covariance R(2,2) calculated through Equation (7), a covariance $\hat{R}(2,2)$ with enhanced stability may be expressed as Equation (9).

$$\hat{R}(2,2) = R(2,2) + 0.01I \qquad (9)$$

Therefore, the weight calculation unit 120 performs operations based on the above-defined equation, and calculates a weight α that is used to synthesize a high resolution image signals.

Herein, when three low resolution image signals are used, the weight α may be a 3×1 matrix. In the matrix, a first row may be a weight for a first low resolution image signal, a second row may be a weight for a second low resolution image signal, and a third row may be a weight for a third low resolution image signal.

Thus, the weight α calculated by the weight calculation unit 120 may be an i×1 type of matrix. In the matrix, an ith row indicates a weight for an ith low resolution image signal.

Accordingly, by performing operations such as Equations (2), (4), and (8), the weight calculation unit 120 may calculate a weight, which is used to synthesize a high resolution image signal, for a signal value corresponding to each of the positions of some pixels among signal values corresponding to respective positions of pixels forming each of the low resolution images.

When synthesizing a high resolution image signal with a plurality of low resolution image signals, a weight may be applied to each of the low resolution image signals. In this case, as a method of calculating the weight, a fixed apodization windowing technique or a data-dependent technique may be used.

As an example of the fixed apodization windowing technique, the fixed apodization windowing technique may use a fixed value (for example, one, etc.) as a weight between a plurality of low resolution image signals, as in a method that accumulates signal values for a pixel in the same position among pixels forming all low resolution images and calculates an average value by using a rectangular window apodization. As another example, the fixed apodization windowing technique may use a Hamming window. In this case, the number of operations may be reduced, but the quality of a diagnosis image is degraded.

As an example of the data-dependent technique, the data-dependent technique calculates an apodization weight for each of all signal values forming all low resolution image signals. The calculating of the apodization weight for all the signal values may be to calculate minimum variance weights based on the minimum variance technique with correlation, for signal values corresponding to respective positions of pixels forming all low resolution images. In this case, the resolution of a diagnosis image is enhanced, and thus, the quality of the diagnosis image is improved. However, the number of operations increases rapidly.

Therefore, as described above, the weight calculation unit 120 calculates a weight for each of a plurality of low resolution images, for a signal value that corresponds to each of the positions of some pixels among signal values corresponding to respective positions of pixels forming each of the low resolution images. Therefore, the number of operations performed by the diagnosis image generation apparatus 100 may be reduced, and moreover, the quality of a diagnosis image may be guaranteed.

As an example, a point indicated by a signal value that corresponds to a position of a pixel in each low resolution image applying a weight is the physically same position, in synthesizing of a high resolution image signal. Therefore, even when a weight for a signal value that corresponds to each of the positions of some pixels among signal values corresponding to respective positions of pixels forming each of a plurality of low resolution images is calculated and a high resolution image signal is synthesized using the calculated weight, the performance of the high resolution image signal is not affected.

Figure 3:
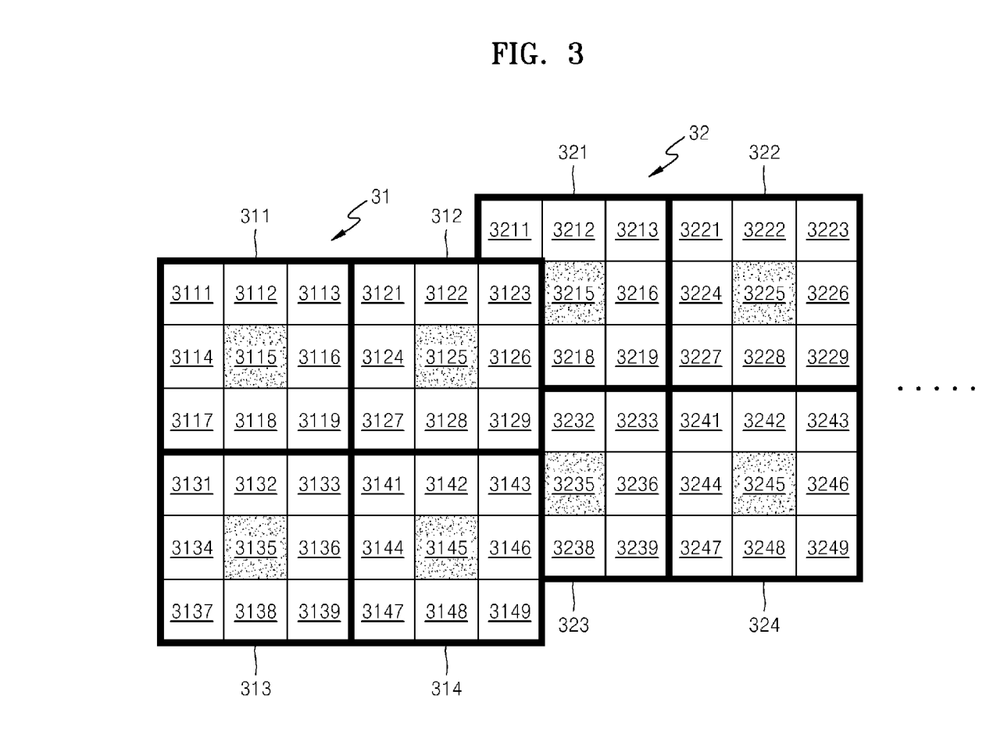
FIG. 3 is a diagram illustrating an example of a method for calculating a weight with a signal value which corresponds to each of the positions of some pixels among signal values corresponding to respective positions of pixels forming a low resolution image, in a weight calculation unit.

In calculating a weight for a signal value that corresponds to each of the positions of some pixels among signal values corresponding to respective positions of pixels forming each of a plurality of low resolution images with the weight calculation unit 120, an example is provided with reference to FIG. 3 on a signal value corresponding to a position of each of some pixels.

As described above, the weight calculation unit 120 calculates a weight for each of a plurality of low resolution image signals, for a signal value that corresponds to each of the positions of some pixels among signal values corresponding to respective positions of pixels forming each of the low resolution images. Accordingly, the number of operations performed by the diagnosis image generation apparatus 100 may be reduced, and moreover, the quality of a diagnosis image may be guaranteed.

The high resolution image signal synthesis unit 130 synthesizes the high resolution image signal by applying the weight calculated by the weight calculation unit 120 for the low resolution image signals. The synthesized high resolution image signal may be generated as a diagnosis image.

The high resolution image signal synthesis unit 130 performs an operation of generating one or more high resolution image signals by applying the weight calculated by the weight calculation unit 120, for the low resolution image signals synthesized by the low resolution image signal synthesis unit 110.

As an example of where a signal is transmitted from the transducers to the subject I times, an operation performed by the high resolution image signal synthesis unit 130 may be expressed as Equation (10).

$$\hat{b}(\vec{r}_p) \cong \sum_{i=0}^{I-1} \alpha_i \cdot l_i(\vec{r}_p) \qquad (10)$$

where $\hat{b}(\vec{r}_p)$ is a signal value for a pixel in a position $\vec{r}_p$ among signal values corresponding to respective positions of pixels forming a high resolution image, $\alpha_i$ is a weight for the $i^{th}$ low resolution image signal calculated through Equation (2), and $l_i(\vec{r}_p)$ is a signal value for a pixel in a position $\vec{r}_p$ of the $i^{th}$ low resolution image calculated through Equation (1).

Accordingly, the number of operations performed by the diagnosis image generation apparatus 100 may be considerably reduced, and moreover, a high definition diagnosis image may be generated.

FIG. 3 is a diagram illustrating an example of a method for calculating a weight with a signal value which corresponds to each of the positions of some pixels among signal values corresponding to respective positions of pixels forming a low resolution image, in the weight calculation unit 120. In FIG. 3, as an example, a case where signal values corresponding to respective positions of pixels forming a low resolution image are brightness values of the pixels forming the low resolution image is described below.

In FIG. 3, low resolution images 31 and 32, pixels 3111 to 3119, 3121 to 3129, 3131 to 3139, and 3141 to 3149 forming the low resolution image 31, and pixels 3211 to 3219, 3221 to 3229, 3231 to 3239, and 3241 to 3249 forming the low resolution image 32 are illustrated.

Referring to FIGS. 2 and 3, the weight calculation unit 120 divides the low resolution image 31 into four regions, namely, first to fourth regions 311 to 314, and divides the low resolution image 32 into four regions, namely, first to fourth regions 321 to 324. The weight calculation unit 120 calculates a weight with a signal value corresponding to a position of any one pixel included in each of the divided regions.

A signal value corresponding to a position of any one pixel may be a signal value of a pixel disposed at the center, a signal value of a first pixel, a signal value of the last pixel, or the like among signal values for pixels included in each region. Hereinafter, as a non-limiting example, the signal value of the pixel disposed at the center will be described.

The weight calculation unit 120 divides the low resolution image 31 into the four regions, namely, the first to fourth regions 311 to 314, and divides the low resolution image 32 into the four regions, namely, the first to fourth regions 321 to 324. The weight calculation unit 120 calculates a first weight for the first region 311 of the low resolution image 31 and a second weight for the first region 321 of the low resolution image 32, by using signal values of the pixels 3115 and 3215 disposed at the center among signal values that correspond to positions of the pixels 3111 to 3119 included in the first region 311 and positions of the pixels 3211 to 3219 included in the first region 321, respectively. The weight calculation unit 120 applies the first weight to the signal values that correspond to the positions of the pixels 3111 to 3119 included in the first region 311 of the low resolution image 31, and applies the second weight to the signal values that correspond to the positions of the pixels 3211 to 3219 included in the first region 321 of the low resolution image 32.

Moreover, the weight calculation unit 120 calculates a third weight for the second region 312 of the low resolution image 31 and a fourth weight for the second region 322 of the low resolution image 32, by using signal values of the pixels 3125 and 3225 disposed at the center among signal values that correspond to positions of the pixels 3121 to 3129 included in the second region 312 and positions of the pixels 3221 to 3229 included in the second region 322, respectively. The weight calculation unit 120 applies the third weight to the signal values that correspond to the positions of the pixels 3121 to 3129 included in the second region 312 of the low resolution image 31, and applies the fourth weight to the signal values that correspond to the positions of the pixels 3221 to 3229 included in the second region 322 of the low resolution image 32.

In this way, the weight calculation unit 120 may calculate a weight that will be applied to the third regions 313 and 323 and the fourth regions 314 and 324.

Therefore, the weight calculation unit 120 divides each of the low resolution images 31 and 32 into a plurality of regions, and calculates a weight with a signal value that corresponds to a position of any one pixel included in each of the regions. The high resolution image signal synthesis unit 130 synthesizes a high resolution image signal by applying the calculated weight to a region including a pixel corresponding to a signal value that has been used to calculate the weight.

As another example, FIG. 3 merely illustrates a non-limiting example. It is understood as being within the scope of the teachings herein that a weight may be calculated with signal values corresponding to respective positions of some pixels (for example, 3119 and 3219) which have been selected at random without division of regions for the low resolution images 31 and 32.

Therefore, the diagnosis image generation apparatus 100 calculates a data-dependent weight and uses the same weight for physically similar positions. Accordingly, the number of operations may be reduced, and a high definition diagnosis may be generated.

Figure 4:
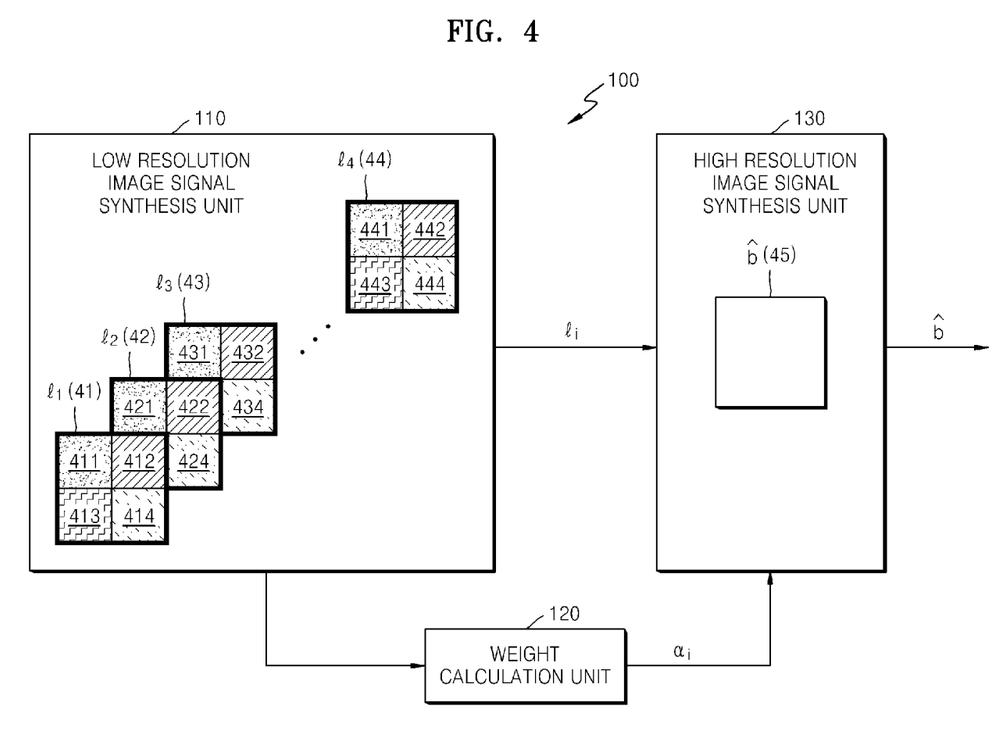
FIG. 4 is a diagram illustrating an example of a method for calculating a weight to synthesize a high resolution image signal in a weight calculation unit.

FIG. 4 is a diagram illustrating an example of a method for calculating a weight to synthesize a high resolution image signal in the weight calculation unit 120. As a non-limiting example, a case where the low resolution image signal synthesis unit 110 synthesizes each of four low resolution image signals and the weight calculation unit 120 divides each low resolution image into four regions has been described. As another non-limiting example, it is assumed that signal values corresponding to respective positions of pixels forming each low resolution image indicate brightness values of pixels included in each low resolution image. It is understood that other implementations are within the scope of the teachings herein.

Referring to FIGS. 2 and 4, the low resolution image signal synthesis unit 110 respectively synthesizes a first low resolution image 41, a second low resolution image 42, a third low resolution image 43, and a fourth low resolution image 44 by using a signal received from each of the transducers.

The weight calculation unit 120 calculates a weight, which is used to synthesize a high resolution image signal, with a signal value that corresponds to each of the positions of some pixels among signal values corresponding to respective positions of pixels forming each of the low resolution images, namely, the first to fourth low resolution images 41 to 44.

As an example, the weight calculation unit 120 divides each of the low resolution images, namely, the first to fourth low resolution images 41 to 44 into four regions and calculates a weight with a signal value that corresponds to a position of any one pixel included in each of the regions.

In other words, the weight calculation unit 120 calculates a weight with a signal value that corresponds to a position of any one pixel included in each of first regions 411, 421, 431, and 441 of the respective low resolution images, namely, the first to fourth low resolution images 41 to 44, and the weight calculation unit 120 allows the calculated weight to be applied to the first regions 411, 421, 431, and 441 including a pixel corresponding to a signal value that has been used to calculate the weight.

As an example, the weight calculation unit 120 calculates first to fourth weights for the respective low resolution images, namely, the first to fourth low resolution images 41 to 44, by using a signal value that corresponds to a position of any one pixel included in the first region 411 of the first low resolution image 41, a signal value that corresponds to a position of any one pixel included in the first region 421 of the second low resolution image 42, a signal value that corresponds to a position of any one pixel included in the first region 431 of the third low resolution image 43, and a signal value that corresponds to a position of any one pixel included in the first region 441 of the fourth low resolution image 44.

Therefore, the high resolution image signal synthesis unit 130 synthesizes a high resolution image 45 by applying the calculated weight for each of the low resolution images, namely, the first to fourth low resolution images 41 to 44.

As an example, a first weight calculated by the weight calculation unit 120 is at least once applied to signal values corresponding to respective positions of pixels included in the first region 411 of the first low resolution image 41. A second weight calculated by the weight calculation unit 120 is at least once applied to signal values corresponding to respective positions of pixels included in the first region 421 of the second low resolution image 42. A third weight calculated by the weight calculation unit 120 is at least once applied to signal values corresponding to respective positions of pixels included in the first region 431 of the third low resolution image 43. A third weight calculated by the weight calculation unit 120 is at least once applied to signal values corresponding to respective positions of pixels included in the first region 441 of the fourth low resolution image 44.

In this way, the weight calculation unit 120 calculates a weight that is used to synthesize a high resolution image signal, and the high resolution image signal synthesis unit 130 synthesizes a high resolution image signal by applying the calculated weight for each of the low resolution image signals.

Therefore, the diagnosis image generation apparatus 100 may efficiently generate a high definition diagnosis image.

Figure 5:
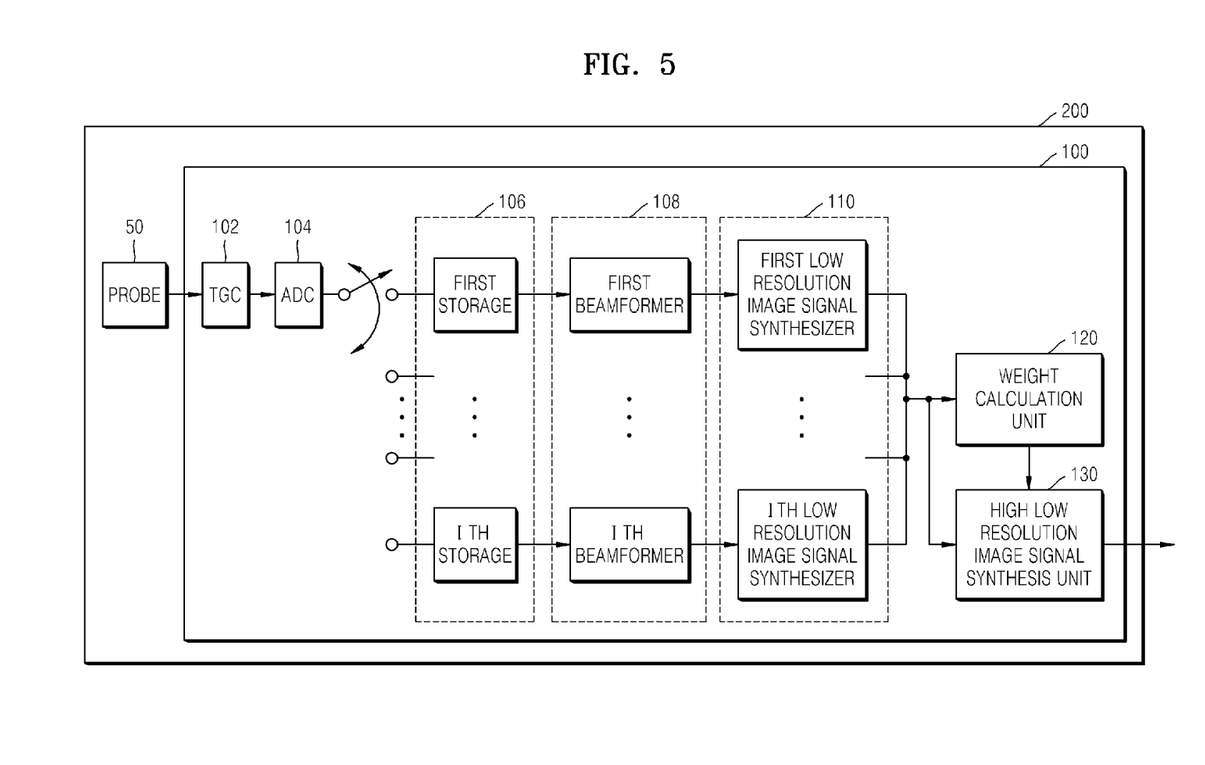
FIG. 5 is a diagram illustrating an example of a diagnosis system.

FIG. 5 is a diagram illustrating an example of a diagnosis system 200. The diagnosis system 200 includes the probe 50 and the diagnosis image generation apparatus 100. The diagnosis image generation apparatus 100 includes a Time Gain Compensation (TGC) 102, an analog-to-digital converter (ADC) 104, a storage unit 106, a beamformer 108, the low resolution image signal synthesis unit 110, the weight calculation unit 120, and the high resolution image signal synthesis unit 130. Also, the storage unit 106 may include first to $I^{th}$ storages, the beamformer 108 may include first to $I^{th}$ beamformers, and the low resolution image signal synthesis unit 110 may include first to $I^{th}$ low resolution image signal synthesizers.

In FIG. 5, as a non-limiting example, a signal is transmitted/received between the probe 50 and a subject I times, according to which a case where an I number of low resolution image signals are generated has been described above.

The diagnosis system 200 of FIG. 5 illustrates elements related to the example. It is understood as being within the scope of the teachings herein that the diagnosis system 200 may further include general elements other than the elements of FIG. 5.

Moreover, the diagnosis image generation apparatus 100 of FIG. 5 corresponds to the example of the diagnosis image generation apparatus 100 of FIGS. 1 and 2. Therefore, the diagnosis image generation apparatus 100 is not limited to the elements of FIG. 5. Also, the description associated with FIGS. 1 to 4 may apply to the diagnosis image generation apparatus 100 of FIG. 5, and thus, repetitive description is not provided.

In the diagnosis system 200, the diagnosis image generation apparatus 100 generates a diagnosis image for a subject by using a signal transmitted/received between the subject and the probe 50. Herein, as a non-limiting example, the signal transmitted/received between the subject and the probe 50 may be an ultrasonic signal, and a diagnosis image of the subject may be an ultrasonic image.

The probe 50 transmits/receives a signal to/from the subject with a plurality of transducers. Herein, the transducers may be an array transducer. As an example, where a signal transmitted/received in the probe 50 is an ultrasonic signal, each of the transducers in the probe 50 converts an electric signal into an ultrasonic signal to transmit the converted ultrasonic signal to the subject, receives the ultrasonic signal reflected by the subject, and converts the received ultrasonic signal into an electric signal.

With signals received from the probe 50, the diagnosis image generation apparatus 100 synthesizes each of a plurality of low resolution image signals, synthesizes a high resolution image signal by applying a predetermined weight to the synthesized low resolution image signals, and outputs the synthesized high resolution image signal as a diagnosis image.

The TGC 102 compensates signal attenuation based on a distance for a signal received from the probe 50. As an example of where a signal is an ultrasonic signal, an ultrasonic beam has characteristics where the ultrasonic beam is transmitted and attenuated according to a depth. Therefore, a signal reflected from a part far away from a surface of the probe 50 is relatively weaker than a signal reflected from a part close to a surface of the probe 50, and thus, an image based on the signal reflected from the part far away from the surface of the probe 50 is displayed dark. Accordingly, the TGC 102 compensates signal attenuation due to a depth and thus allows signals reflected from different parts of the subject to be displayed at the same brightness.

The ADC 102 converts a signal corrected by the TGC 102 into a digital signal.

The storage unit 106 stores the digital signal that has been converted by the ADC 104. Herein, the storage unit 106 may include the first to $I^{th}$ storages.

In a case where the transducers included in the array transducer sequentially transmit a signal, the first transducer of the transducers transmits a signal to the subject, and each of the transducers receives a signal reflected from the subject. The received signal is stored in the first storage of the storage unit 106 through the TGC 102 and ADC 104.

The second transducer of the transducers transmits a signal to the subject, and each of the transducers receives a signal reflected from the subject. The received signal is stored in the second storage of the storage unit 106 through the TGC 102 and ADC 104.

The $I^{th}$ transducer of the transducers transmits a signal to the subject, and each of the transducers receives a signal reflected from the subject. The received signal is stored in the $I^{th}$ storage of the storage unit 106 through the TGC 102 and ADC 104.

It is understood that the storage unit 106 as a general storage medium may include a Hard Disk Drive (HDD), a Read Only Memory (ROM), a Random Access Memory (RAM), a flash memory, and a memory card.

The beamformer 108 and the low resolution image signal synthesis unit 110 synthesize each of a plurality of low resolution image signals with a signal stored in the storage unit 106.

Herein, the beamformer 108 may include the first to $I^{th}$ beamformers, and the low resolution image signal synthesis unit 110 may include the first to $I^{th}$ low resolution image signal synthesizers. The first to $I^{th}$ low resolution image signal synthesizers synthesize a plurality of low resolution image signals, respectively.

Moreover, as a non-limiting example, FIG. 5 illustrates that the beamformer 108 is included independently from the low resolution image signal synthesis unit 110. However, as another example, it is understood that the beamformer 108 may be included in the low resolution image signal synthesis unit 110.

The weight calculation unit 120 calculates a weight, which is used to synthesize a high resolution image signal, with a signal value that corresponds to each of the positions of some pixels among signal values corresponding to respective positions of pixels forming each of the low resolution images. The weight calculation unit 120 calculates a weight with a signal value that corresponds to each of the positions of some pixels among signal values corresponding to respective positions of pixels forming the first to $I^{th}$ low resolution images which have respectively been synthesized by the first to $I^{th}$ low resolution image signal synthesizers.

The high resolution image signal synthesis unit 130 synthesizes the high resolution image signal by respectively applying the weights calculated by the weight calculation unit 120 to the low resolution image signals synthesized by the low resolution image signal synthesis unit 110.

In the above example, the storage unit 106, the beamformer 108, and the low resolution image signal synthesis unit 110 may be included in one hardware unit. Also, the first to $I^{th}$ storages, the first to $I^{th}$ beamformers, and the first to $I^{th}$ low resolution image signal synthesizers may be included in respective virtual spaces divided in one hardware unit.

However, as another example, the storage unit 106, the beamformer 108, and the low resolution image signal synthesis unit 110 may be included in a plurality of hardware units that respectively correspond to the first to $I^{th}$ storages, the first to $I^{th}$ beamformers, and the first to $I^{th}$ low resolution image signal synthesizers, respectively.

As described above, the diagnosis image generation apparatus 100 synthesizes the high resolution image signal by applying the weight that has been calculated with a signal value which corresponds to each of the positions of some pixels among signal values corresponding to respective positions of pixels forming each of the low resolution images. Accordingly, the number of operations performed by the diagnosis image generation apparatus 100 may be considerably reduced, and moreover, the quality of the generated high resolution image signal may be guaranteed.

Figure 6:
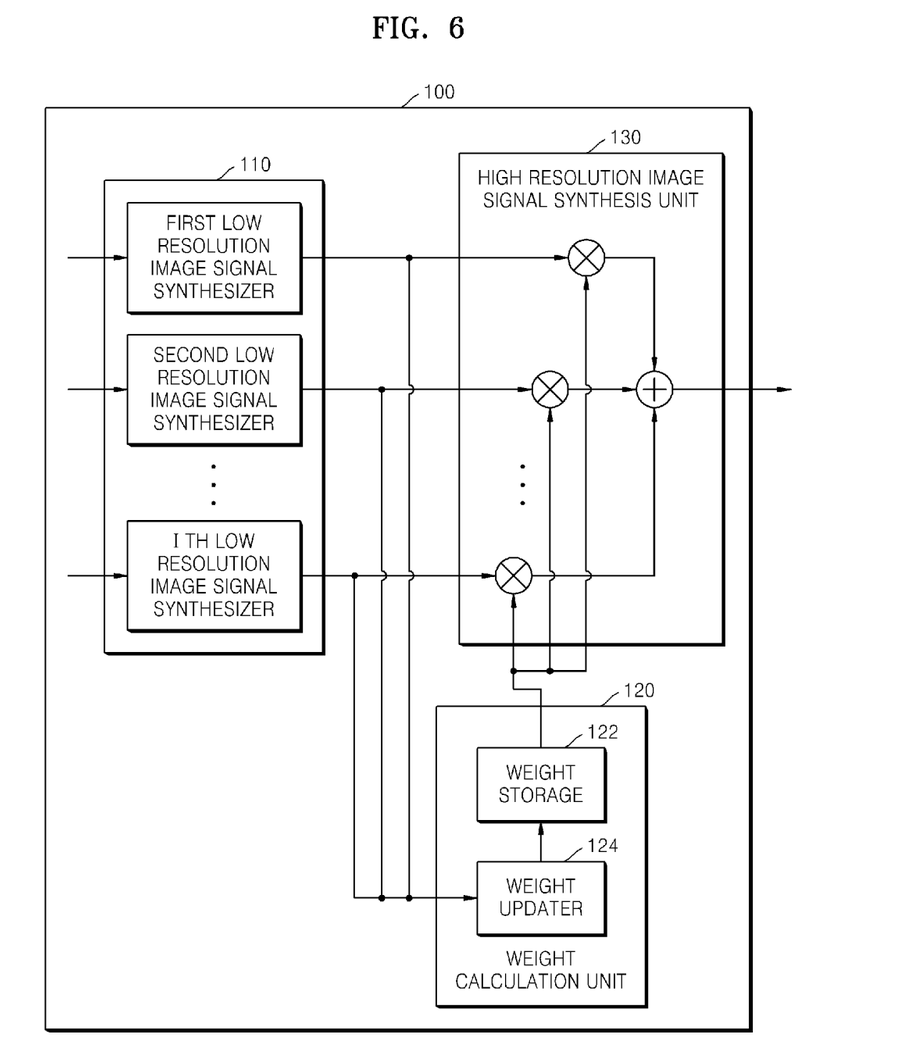
FIG. 6 is a diagram illustrating an example of a weight calculation unit.

FIG. 6 is a diagram illustrating an example of the weight calculation unit 120. Referring to FIG. 6, the weight calculation unit 120 includes a weight storage 122 and a weight updater 124.

A diagnosis image generation apparatus 100 of FIG. 6 corresponds to an example of the diagnosis image generation apparatus 100 of FIGS. 1, 2, and 5. Therefore, the diagnosis image generation apparatus 100 is not limited to the elements of FIG. 6. Also, the description associated with FIGS. 1 to 5 may be applied to the diagnosis image generation apparatus 100 of FIG. 6.

The weight calculation unit 120 calculates a weight, which is used to synthesize a high resolution image signal, with a signal value that corresponds to each of the positions of some pixels among signal values corresponding to respective positions of pixels forming each of the low resolution images that have been synthesized by the low resolution image signal synthesis unit 110.

For example, the weight storage 122 stores the calculated weight. The weight updater 124 calculates a weight with a signal value that corresponds to each of the positions of some pixels among signal values corresponding to respective positions of pixels forming each of the low resolution images, and updates a weight stored in the weight storage 122 to the calculated weight. Herein, the weight stored in the weight storage 122 may be an apodization weight.

As another example, the weight updater 124 updates only a weight that has been calculated with a signal value which corresponds to each of the positions of some pixels among signal values corresponding to respective positions of pixels forming each of the low resolution images. The weight storage 122 stores updated weights, and thus, the high resolution image signal synthesis unit 130 at least once applies the weights stored in the weight storage 122 to a signal value other than signal values, corresponding to respective positions of some pixels which have been used to calculate the weights, among signal values corresponding to respective positions of pixels forming a low resolution image.

As an example with reference to FIG. 3, the weight updater 124 calculates a first weight with a signal value, corresponding to a position of a pixel 3115 among signal values that correspond to respective positions of the pixels 3111 to 3119 forming the first region 311 of the low resolution image 31, and a signal value corresponding to a position of a pixel 3215 among signal values that correspond to respective positions of the pixels 3211 to 3219 forming the first region 321 of the low resolution image 32, and updates a weight stored in the weight storage 122 to a first weight.

At this point, the high resolution image signal synthesis unit 130 synthesizes a high resolution image signal by at least once applying a first weight for the low resolution image 31, which is stored in the weight storage 122, to signal values corresponding to respective positions of the pixels 3111 to 3119 forming the first region 311 of the low resolution image 31.

Moreover, the high resolution image signal synthesis unit 130 synthesizes a high resolution image signal by at least once applying a first weight for the low resolution image 32, which is stored in the weight storage 122, to signal values corresponding to respective positions of the pixels 3211 to 3219 forming the first region 321 of the low resolution image 32.

As another example, the weight updater 124 calculates a first weight with a signal value corresponding to a position of a pixel 3125 among signal values that correspond to respective positions of the pixels 3121 to 3129 forming the second region 312 of the low resolution image 31, and a signal value corresponding to a position of a pixel 3225 among signal values that correspond to respective positions of the pixels 3221 to 3229 forming the second region 322 of the low resolution image 32, and updates a weight stored in the weight storage 122 to a second weight.

At this point, the high resolution image signal synthesis unit 130 synthesizes a high resolution image signal by at least once applying a second weight for the low resolution image 31, which is stored in the weight storage 122, to signal values corresponding to respective positions of the pixels 3121 to 3129 forming the second region 312 of the low resolution image 31.

Moreover, the high resolution image signal synthesis unit 130 synthesizes a high resolution image signal by at least once applying a second weight for the low resolution image 32, which is stored in the weight storage 122, to signal values corresponding to respective positions of the pixels 3221 to 3229 forming the second region 322 of the low resolution image 32.

Such operations are at least once performed by the weight storage 122 and the weight updater 124, and thus, the high resolution image signal synthesis unit 130 may acquire a high definition and resolution image signal.

Figure 7:
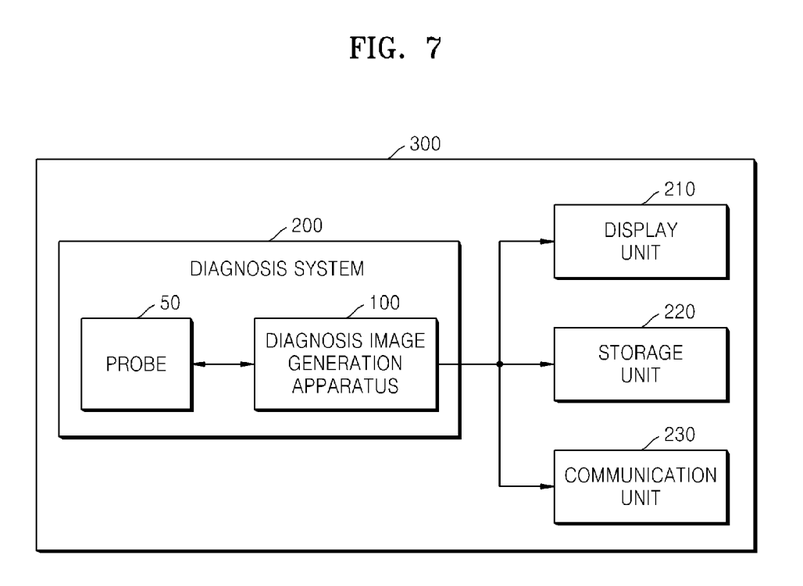
FIG. 7 is a diagram illustrating an example of a medical image system.

FIG. 7 is a diagram illustrating an example of a medical image system 300. Referring to FIG. 7, the medical image system 300 includes the diagnosis system 200, a display unit 210, a storage unit 220, and a communication unit 230. The diagnosis system 200 includes the probe 50 and the diagnosis image generation apparatus 100.

In the medical image system 300 of FIG. 7, elements associated with this example are illustrated. It is understood as being within the scope of the teachings herein that the medical image system 300 may further include general elements other than the elements of FIG. 7.

Moreover, the probe 50, the diagnosis image generation apparatus 100 and the diagnosis system 200 of FIG. 7 correspond to an example of the probe 50, the diagnosis image generation apparatus 100, and the diagnosis system 200 of FIGS. 1, 2, 5, and 6, respectively. Therefore, the description associated with FIGS. 1 to 6 may apply to the medical image system 300 of FIG. 7.

The diagnosis system 200 synthesizes each of a plurality of low resolution image signals by using signals received from the transducers, synthesizes a high resolution image signal by applying a weight, which has been calculated with a signal value that corresponds to each of positions of some pixels among signal values corresponding to respective positions of pixels forming each of the synthesized low resolution image signals, to each of the low resolution image signals, and outputs the synthesized high resolution image signal as a diagnosis image.

Therefore, the probe 50 transmits/receives a signal to/from a subject with the transducers. The diagnosis image generation apparatus 100 synthesizes each of a plurality of low resolution image signals by using signals received from the probe 50, synthesizes a high resolution image signal by applying a weight, which has been calculated with a signal value that corresponds to each of positions of some pixels among signal values corresponding to respective positions of pixels forming each of the synthesized low resolution image signals, to the low resolution image signals, and outputs the synthesized high resolution image signal as a diagnosis image.

The display unit 210 displays the diagnosis image outputted from the diagnosis system 200. For example, the display unit 210 includes output devices such as a display panel, a touch screen, and a monitor that are included in the medical image system 300, and a plurality of software modules for respectively driving the output devices.

The storage unit 220 stores the diagnosis image outputted from the diagnosis system 200. For example, the storage unit 220 as a general storage medium may include a HDD, a ROM, a RAM, a flash memory, and a memory card.

The communication unit 230 transmits the diagnosis image, outputted from the diagnosis system 200, to an external device and receives data from the external device. Herein, the external device may be a fax machine, a general computer system, or another medical image system that is disposed external to the medical image system 300.

The communication unit 230 may transmit/receive data to/from an external device over a wired/wireless network. As a non-limiting example, the network includes the Internet, a Local Area Network (LAN), a wireless LAN, a Wide Area Network (WAN), and a Personal Area Network (PAN). It is within the scope of the teachings herein that the network may be another type of network for transmitting/receiving information.

Moreover, it is within the scope of the teachings herein that the storage unit 220 and the communication unit 230 may be integrated in a type such as a Picture Archiving Communication System (PACS) by further adding an image read function and a search function.

Therefore, the medical image system 300 may display, store, and transmit a diagnosis image that is generated and outputted by the diagnosis image generation apparatus 200.

Figure 8:
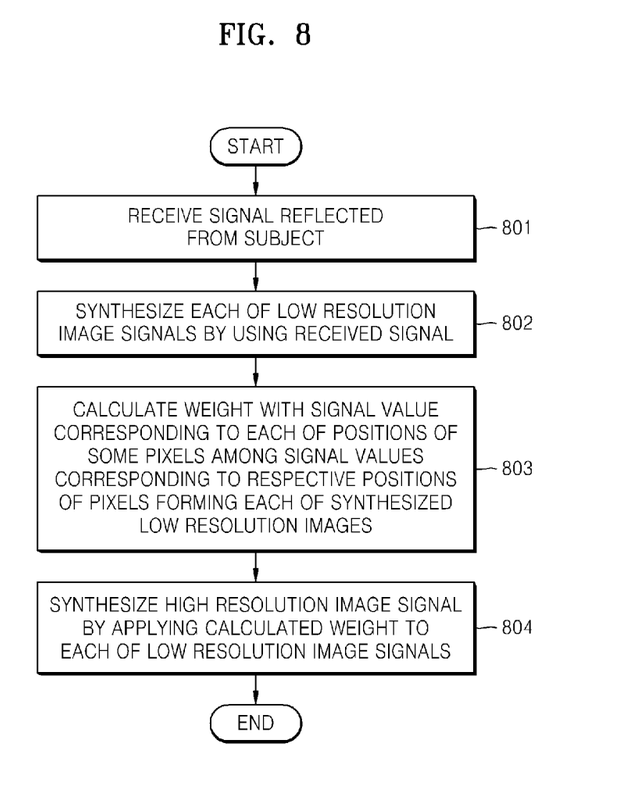
FIG. 8 is a flowchart illustrating an example of a method of generating an image.

FIG. 8 is a flowchart illustrating an example of a method of generating a diagnosis image. Referring to FIG. 8, the method includes a plurality of operations that may be time-series processed in the probe 50 and the diagnosis image generation apparatus 100 of FIGS. 1, 2, and 5 to 7 and the medical image system 300 of FIG. 7. Therefore, it is within the scope of the teachings herein that the descriptions associated with the probe 50 and the diagnosis image generation apparatus 100 of FIGS. 1, 2, and 5 to 7 and the medical image system 300 of FIG. 7 may apply to the method of FIG. 8.

In operation 801, the probe 50 receives signals reflected from a subject. Herein, the signal reflected from the subject indicates a signal that is transmitted by the probe 50 and reflected by the subject.

In operation 802, the low resolution image signal synthesis unit 110 synthesizes each of a plurality of low resolution image signals by using the signal that has been received in operation 801.

In operation 803, the weight calculation unit 120 calculates a weight, which is used to synthesize a high resolution image signal, with a signal value that corresponds to each of the positions of some pixels among signal values corresponding to respective positions of pixels forming each of the low resolution images that have been synthesized in operation 802. The calculated weight may be stored, and in response to a new weight being calculated, the stored weight may be updated.

In operation 804, the high resolution image signal synthesis unit 130 synthesizes a high resolution image signal by applying the weight, which has been calculated in operation 803, to each of the low resolution image signals that have been synthesized in operation 802. Accordingly, the synthesized high resolution image signal may be generated and outputted as a diagnosis image.

Therefore, the diagnosis image generation apparatus 100 applies different weights to pixels forming a plurality of the low resolution image signals in synthesizing of a high resolution image signal. Accordingly, the number of operations may be considerably reduced, and moreover, the performance of a high resolution image signal may be guaranteed.

As described above, according to the one or more of the above examples, the performance of a generated diagnosis image may be guaranteed and the number of operations may be reduced.

Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable recording mediums. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein. Also, the described unit to perform an operation or a method may be hardware, software, or some combination of hardware and software. For example, the unit may be a software package running on a computer or the computer on which that software is running.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A diagnosis image generation apparatus comprising:
a low resolution image signal synthesis unit configured to synthesize each of a plurality of low resolution image signals by using a signal reflected from a subject;
a weight calculation unit configured to calculate a weight, which is used to synthesize a high resolution image signal, with a signal value which corresponds to each of positions of some pixels among a plurality of signal values corresponding to respective positions of a plurality of pixels forming each of the synthesized low resolution image signals; and
a high resolution image signal synthesis unit configured to synthesize the high resolution image signal by applying the calculated weight to each of the low resolution image signals.

2. The diagnosis image generation apparatus of claim 1, wherein,
the weight calculation unit divides each of the low resolution image signals into a plurality of regions, and calculates a weight with a signal value corresponding to a position of one pixel included in each of the regions, and
the high resolution image signal synthesis unit applies the calculated weight to a region including the pixel corresponding to the signal value which has been used to calculate the weight.

3. The diagnosis image generation apparatus of claim 1, wherein the weight calculation unit calculates the weight for the signal value which corresponds to each of the positions of some pixels included in each of the low resolution image signals, in a minimum variance technique.

4. The diagnosis image generation apparatus of claim 3, wherein the weight calculation unit generates a covariance matrix for a signal value which corresponds to each of the positions of some pixels included in each of the low resolution image signals, calculates an inverse of the generated covariance matrix, and calculates a weight with the calculated inverse of the covariance matrix.

5. The diagnosis image generation apparatus of claim 1, wherein the weight calculation unit comprises:
a weight storage configured to store the calculated weight; and
a weight updater configured to calculate a weight which is used to synthesize the high resolution image signal, and configured to update the weight, stored in the weight storage, to the calculated weight.

6. The diagnosis image generation apparatus of claim 5, wherein the high resolution image signal synthesis unit at least once applies the weights, stored in the weight storage, to a signal value other than the signal values, corresponding to each of the positions of some pixels which have been used to calculate the weight, among signal values corresponding to respective positions of the pixels forming the low resolution image signals.

7. The diagnosis image generation apparatus of claim 1, wherein the weight corresponds to an apodization weight.

8. A diagnosis system comprising:
a probe configured to transmit/receive a signal to/from a subject by using a plurality of transducers; and
a diagnosis image generation apparatus synthesizing each of a plurality of low resolution image signals with signals received from the probe, configured to synthesize a high resolution image signal by applying a weight, which is calculated with a signal value which corresponds to each of positions of some pixels among a plurality of signal values corresponding to respective positions of a plurality of pixels forming each of the synthesized low resolution image signals, to each of the low resolution image signals, and configured to output the synthesized high resolution image signal as a diagnosis image.

9. The diagnosis system of claim 8, wherein the diagnosis image generation apparatus divides each of the low resolution image signals into a plurality of regions, and calculates a weight with a signal value corresponding to a position of one pixel included in each of the regions, and applies the calculated weight to a region including the pixel corresponding to the signal value which has been used to calculate the weight.

10. A medical image system comprising:
a diagnosis image generation apparatus configured to synthesize each of a plurality of low resolution image signals by using a signal reflected from a subject, configured to synthesize a high resolution image signal by applying a weight, which is calculated with a signal value which corresponds to each of positions of some pixels among a plurality of signal values corresponding to respective positions of a plurality of pixels forming each of the synthesized low resolution image signals, to each of the low resolution image signals, and configured to output the synthesized high resolution image signal as a diagnosis image; and
a display unit configured to display the output diagnosis image.

11. The medical image system of claim 10, wherein the diagnosis image generation apparatus divides each of the low resolution image signals into a plurality of regions, and calculates a weight with a signal value corresponding to a position of one pixel included in each of the regions, and applies the calculated weight to a region including the pixel corresponding to the signal value which has been used to calculate the weight.

12. A method of generating a diagnosis image, the method comprising:
receiving a signal reflected from a subject by a probe;
synthesizing each of a plurality of low resolution image signals from a low resolution image signal synthesis unit by using the received signal;
calculating a weight by a weight calculation unit, which is used to synthesize a high resolution image signal, with a signal value which corresponds to each of positions of some pixels among a plurality of signal values corresponding to respective positions of a plurality of pixels forming each of the synthesized low resolution image signals; and synthesizing the high resolution image signal by applying the calculated weight to each of the low resolution image signals.

13. The method of claim 12, wherein,
the calculating of the weight divides each of the low resolution image signals into a plurality of regions, and calculates a weight with a signal value corresponding to a position of one pixel included in each of the regions, and
the synthesizing of the high resolution image signal applies the calculated weight to a region including the pixel corresponding to the signal value which has been used to calculate the weight.

14. The method of claim 12, wherein the calculating of the weight calculates the weight for the signal value which corresponds to each of positions of some pixels included in each of the low resolution image signals, in a minimum variance technique.

15. The method of claim 14, wherein the calculating of the weight generates a covariance matrix for a signal value which corresponds to each of positions of some pixels included in each of the low resolution image signals, calculates an inverse of the generated covariance matrix, and calculates a weight with the calculated inverse of the covariance matrix.

16. The method of claim 12, wherein the calculating of the weight comprises:
calculating the weight which is used to synthesize the high resolution image signal;
storing the calculated weight; and
updating the stored weight to the calculated weight.

17. The method of claim 16, wherein the synthesizing of the high resolution image signal at least once applies the stored weights to a signal value other than the signal values, corresponding to each of the positions of pixels which have been used to calculate the weight, among signal values corresponding to respective positions of the pixels forming the low resolution image signals.

18. The method of claim 12, wherein the weight corresponds to an apodization weight.

19. The method of claim 12, further comprising displaying the synthesized high resolution image signal as a diagnosis image.

20. A non-transitory computer-readable storage medium storing a computer program for executing the method of claim 12.

* * * * *